(12) United States Patent
Rottenberg et al.

(10) Patent No.: US 11,083,870 B2
(45) Date of Patent: Aug. 10, 2021

(54) HYPOTUBE BASED SUPPORT CATHETER

(75) Inventors: Dan Rottenberg, Haifa (IL); Ron Sacher, Herzelia (IL)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 0 days.

(21) Appl. No.: 13/390,140

(22) PCT Filed: Dec. 12, 2011

(86) PCT No.: PCT/US2011/064300
§ 371 (c)(1),
(2), (4) Date: Feb. 13, 2012

(87) PCT Pub. No.: WO2012/141747
PCT Pub. Date: Oct. 18, 2012

(65) Prior Publication Data
US 2014/0031843 A1 Jan. 30, 2014

Related U.S. Application Data

(60) Provisional application No. 61/516,906, filed on Apr. 11, 2011, provisional application No. 61/571,856,
(Continued)

(51) Int. Cl.
*A61M 25/00* (2006.01)
*A61M 25/01* (2006.01)
(Continued)

(52) U.S. Cl.
CPC .... *A61M 25/0054* (2013.01); *A61M 25/0138* (2013.01); *A61B 17/22* (2013.01);
(Continued)

(58) Field of Classification Search
CPC .......... A61M 25/0013; A61M 25/0051; A61M 25/0054
(Continued)

(56) References Cited

U.S. PATENT DOCUMENTS 4,860,742 A   8/1989   Park
5,116,323 A   5/1992   Kreuzer
(Continued)

FOREIGN PATENT DOCUMENTS

EP   0257811   3/1988
EP   0342505   11/1989
(Continued)

OTHER PUBLICATIONS

International Search Report for International Patent Application No. PCT/US2011/064300, dated Dec. 19, 2012 4 pages.
(Continued)

*Primary Examiner* — Sarah W Aleman

(57) ABSTRACT

Hypo-tube based support catheter (1) for treating blood vessels, such as below the knee (BTK) blood vessels and other blood vessels (e.g., coronary, pediatric), which are partially or totally occluded. The tip of the support catheter (1) of the invention is shapeable to any desired shape before the insertion of the device into the blood vessel. The disclosed device enables improved angioplasty treatment of blood vessels, especially with a retrograde approach.

8 Claims, 3 Drawing Sheets

Related U.S. Application Data filed on Jul. 7, 2011, provisional application No. 61/575,160, filed on Aug. 17, 2011, provisional application No. 61/573,935, filed on Sep. 15, 2011, provisional application No. 61/626,183, filed on Sep. 22, 2011.

(51) Int. Cl.
*A61M 25/06* (2006.01)
*A61B 17/22* (2006.01)

(52) U.S. Cl.
CPC ............... *A61B 2017/22001* (2013.01); *A61B 2017/22035* (2013.01); *A61B 2017/22038* (2013.01); *A61B 2017/22094* (2013.01)

(58) Field of Classification Search
USPC .................................................. 604/524, 525
See application file for complete search history.

(56) References Cited

U.S. PATENT DOCUMENTS

| | | | |
|---|---|---|---|
| 5,129,884 | A | 7/1992 | Dysarz |
| 5,295,970 | A | 3/1994 | Clinton |
| 5,489,274 | A | 2/1996 | Chu |
| 5,741,429 | A | 4/1998 | Donadio, III et al. |
| 5,911,715 | A | 6/1999 | Berg et al. |
| 5,984,895 | A | 11/1999 | Padilla |
| 6,290,710 | B1 | 9/2001 | Cryer |
| 6,352,531 | B1 | 3/2002 | O'Connor et al. |
| 6,428,489 | B1 | 8/2002 | Jacobsen et al. |
| 7,097,564 | B2 | 8/2006 | Berg |
| 7,708,704 | B2 * | 5/2010 | Mitelberg et al. ........... 623/1.11 |
| 7,878,984 | B2 | 2/2011 | Jacobsen et al. |
| 8,257,382 | B2 | 9/2012 | Rottenberg et al. |
| 8,257,383 | B2 | 9/2012 | Rottenberg et al. |
| 8,414,568 | B2 | 4/2013 | Harlan |
| 8,758,333 | B2 | 6/2014 | Harlan |
| 9,283,039 | B2 | 3/2016 | Harlan |
| 2001/0018596 | A1 | 8/2001 | Selmon |
| 2004/0082962 | A1 | 4/2004 | Demarais |
| 2005/0245885 | A1 | 11/2005 | Brown |
| 2006/0100687 | A1 * | 5/2006 | Fahey et al. ................. 623/1.11 |
| 2007/0112331 | A1 | 5/2007 | Webler et al. |
| 2007/0225702 | A1 | 9/2007 | Kaouk |
| 2008/0306499 | A1 | 12/2008 | Katoh |
| 2009/0125097 | A1 | 5/2009 | Bruszewski et al. |
| 2009/0270975 | A1 | 10/2009 | Gifford, III et al. |
| 2010/0022943 | A1 | 1/2010 | Mauch |
| 2010/0036364 | A1 | 2/2010 | Wubbeling |
| 2010/0057037 | A1 | 3/2010 | Webler |
| 2012/0265229 | A1 | 10/2012 | Rottenberg et al. |
| 2012/0265233 | A1 | 10/2012 | Waisman et al. |
| 2016/0183765 | A1 | 6/2016 | Harlan |

FOREIGN PATENT DOCUMENTS

| | | |
|---|---|---|
| EP | 0583049 | 2/1994 |
| EP | 0623673 | 11/1994 |
| EP | 0633184 | 1/1995 |
| EP | 0650666 | 5/1995 |
| EP | 0724098 | 7/1996 |
| EP | 0846064 | 6/1998 |
| EP | 0897295 | 2/1999 |
| EP | 0922466 | 6/1999 |
| EP | 1009466 | 6/2000 |
| EP | 1035880 | 9/2000 |
| EP | 1045708 | 10/2000 |
| EP | 1098671 | 5/2001 |
| EP | 1109590 | 6/2001 |
| EP | 1399549 | 3/2004 |
| EP | 1441672 | 8/2004 |
| EP | 1546664 | 6/2005 |
| EP | 1771132 | 4/2007 |
| EP | 1789122 | 5/2007 |
| EP | 1796597 | 6/2007 |
| EP | 2012660 | 1/2009 |
| EP | 2052756 | 4/2009 |
| EP | 2055266 | 5/2009 |
| EP | 2131913 | 12/2009 |
| EP | 2163216 | 3/2010 |
| EP | 2163217 | 3/2010 |
| EP | 2185107 | 5/2010 |
| EP | 2399550 | 12/2011 |
| EP | 2470248 | 7/2012 |
| EP | 2473123 | 7/2012 |
| EP | 2494419 | 9/2012 |
| EP | 2512577 | 10/2012 |
| WO | WO 88/09188 | 12/1988 |
| WO | 94/13211 | 6/1994 |
| WO | WO 97/06973 | 2/1997 |
| WO | WO 98/28034 | 7/1998 |
| WO | WO 98/57694 | 12/1998 |
| WO | WO 99/26676 | 6/1999 |
| WO | WO 99/26677 | 6/1999 |
| WO | WO 00/03754 | 1/2000 |
| WO | WO 00/13736 | 3/2000 |
| WO | 00/20064 | 4/2000 |
| WO | WO 00/37128 | 6/2000 |
| WO | 01/97697 | 12/2001 |
| WO | 03/002182 | 1/2003 |
| WO | WO 03/002734 | 1/2003 |
| WO | WO 03/047468 | 6/2003 |
| WO | WO 2004/025229 | 3/2004 |
| WO | 2005/011792 | 2/2005 |
| WO | WO 2005/028002 | 3/2005 |
| WO | WO 2006/019592 | 2/2006 |
| WO | 2007/011908 | 1/2007 |
| WO | WO 2008/024593 | 2/2008 |
| WO | WO 2008/035349 | 3/2008 |
| WO | WO 2008/120209 | 10/2008 |
| WO | WO 2009/033173 | 3/2009 |
| WO | WO 2010/137024 | 12/2010 |
| WO | WO 2011/025855 | 3/2011 |
| WO | WO 2011/028632 | 3/2011 |
| WO | WO 2011/041578 | 4/2011 |
| WO | WO 2011/051944 | 5/2011 |
| WO | WO 2011/084616 | 7/2011 |

OTHER PUBLICATIONS

International Preliminary Report on Patentability and Written Opinion for International Patent Application No. PCT/US2011/064300, dated Oct. 15, 2013 5 pages.

* cited by examiner

HYPOTUBE BASED SUPPORT CATHETER

CROSS-REFERENCE TO RELATED APPLICATION

This application is the U.S. national stage of PCT/US2011/064300 entitled "HYPOTUBE BASED SUPPORT CATHETER," published as WO 2012/141747, filed Dec. 12, 2011, which claims the benefit under 35, U.S.C. § 119(e) of U.S. Provisional Patent Application Ser. No. 61/516,906, filed Apr. 11, 2011, U.S. Provisional Patent Application Ser. No. 61/571,856, filed Jul. 7, 2011, U.S. Provisional Patent Application Ser. No. 61/575,160, filed Aug. 17, 2011, U.S. Provisional Patent Application Ser. No. 61/573,935, filed Sep. 15, 2011, and U.S. Provisional Patent Application Ser. No. 61/626,183, filed Sep. 22, 2011.

FIELD OF THE INVENTION

The present invention generally relates to support catheters for treating blood vessels, mainly small blood vessels, such as below the knee (BTK) blood vessels and other small blood vessels (e.g., coronary, pediatric), which are partially or totally occluded.

BACKGROUND OF THE INVENTION

A chronic total occlusion (CTO) is an arterial vessel blockage that prevents blood flow beyond the obstruction. CTO' s typically occur in coronary, peripheral, pediatric, and other small arteries. In the coronary and peripheral arteries, they result from the same underlying cause—atherosclerosis.

One of the main difficulties in crossing a total occlusion is that the clinician does not know in advance exactly how hard the plaque will be until he/she advances the guidewire—the most common tool for crossing partial and total occlusions—until reaching the obstruction. If the occlusion is relatively new, the plaque is likely to be soft, and the guidewire should penetrate the plaque and pass through the plaque. If the plaque is several weeks or months old, it becomes much harder as the occlusion becomes fibrotic and calcified, making it hard for guidewire passage. In such a case, a support catheter might be used to support the guidewire penetration through the plaque.

Increasing prevalence of diabetes mellitus is frequently associated with complex tibial-peroneal obstructive disease and a high rate of amputation. Endovascular therapies for arteries below the knee have emerged as a promising revascularization technique for patients with critical limb ischemia (CLI). However, when employing standard angioplasty techniques, angioplasty of BTK arteries fails to achieve revascularization in up to 20% of cases. The main cause for failure is the inability to penetrate the plaque's proximal cap with the guidewire.

A new technique of approaching the plaque from below—known as the retrograde Approach—is often used to pass the guidewire through the plaque from the other direction. This approach has high success rates, but is technically challenging to perform and has its own complications, especially the danger of vessel perforation.

Flexible, small support catheters can be used to support the guidewire crossing the plaque from that direction as well. These support catheters may have straight tips or pre-curved tips suitable for maneuvering through side branched or curved blood vessels.

Currently, treatment of below the knee and other small arteries is usually performed via a cross-over or antegrade approach. In these approaches, the femoral artery, having a diameter of 6 mm to 8 mm, is punctured with a sheath having a diameter of 5 Fr to 8 Fr (1.7 mm-2.7 mm). Such a sheath creates a channel to allow the deployment of different standard tools such as support catheters, balloon catheters and stents.

If during percutaneous transluminal recanalization (PTA) the plaque cannot be crossed with guidewire manipulation, a support catheter can be inserted over the guidewire to support and aim the guidewire tip to the occlusion. The support catheter distal tip is usually straight. Sometimes a pre-curved tip is used, especially if a sharp bend is just before the plaque or the plaque is in a side branch which is hard to enter. The antegrade approach is abandoned in favor of the retrograde approach when the combined support catheter and guidewire technique are ineffective in crossing the plaque. The retrograde approach is the last percutaneous alternative before referring the patient to traditional open surgery.

Several support catheters are commercially available. All accommodate different sizes of guidewires, usually 0.014", 0.018" or 0.035" diameter, and have lumens designed to accommodate the specific guidewire size.

Most support catheters are made from polymer tubes, sometimes braided reinforced tubes. One advantage of such catheters is their low production cost. Another advantage is they provide good flexibility which is required to pass through tortuous and curved small vessels. However, a disadvantage is the pushability of the catheter is relatively low due to the polymer-based structure and small diameters (usual OD range is 0.5-1.5 mm). This is a serious shortcoming as good pushability of the support catheter is required to help the guidewire pass through hard calcified plaques.

Another disadvantage is that polymer tubing, even when reinforced, does not generally attain the torqueability required to aim the guidewire as it exits from the pre-curved tip of a support catheter. The ability of the guidewire to exit at an angle to the main catheter shaft is required many times, due to the curvature of typical blood vessels and tendency of plaques to accumulate at such locations.

Several hypotube-based support catheters are available, such as the TORNUS support catheter from ASAHI. This catheter has a spiral cut (like a spring), to provide very good flexibility, but this comes at the expense of lower pushability. The torqueability of such hypotube-based catheters is usually good in one rotational direction only, but when the spring-cut hypotube rotates, it tends to reduce its diameter, and might lock the guidewire inside.

US Patent Application 2009/0125097 describes a slotted hypotube-based catheter, where slots can be made by laser cuts or other cutting means. The slots are cut alternatively from one direction and then from the other direction, opposite to the first direction, such that every slot is cut 180° from the adjacent cut. Such laser cuts have combined properties of strength and compression resistance, together with very good torqueability, while flexible enough to deal with turns of about 10 mm radius. However, these designs provide flexibility only in one plane, and the catheter must be rotated to its proper position to allow slots width changes (i.e., close at one side and open in other side) when bent in the curve plane. Obviously, such a laser cut profile is not flexible in multi-directions, and can not deal with multiple curves or 3D curves as is in the human vasculature, especially when treating small blood vessels.

U.S. Pat. No. 5,741,429 describes another symmetrical slot cutting approach. This design has more than two rows of slots, so flexibility is in more than one axis. However, the design is still not flexible in every direction, and does not have multi-axis flexibility.

US Patent Application 20090270975 describes a different laser-cut profile, which aims to provide good pushability and torqueability, while keeping multi-axis flexibility and potentially the ability to deal with multiple and 3D curves. This design is based on cut and uncut segments of a general spiral profile. This application describes a hypotube-based catheter which is formed with a plurality of cuts which are not perpendicular to the longitudinal axis of the catheter. The cuts are formed by intermittent cutting of the hypotube, while rotating and advancing it at the same time. Such a design overcomes some of the limitations of previous slotted hypotube-based support catheters, by providing very good pushability and torqueability. However it has limited flexibility due to the spiral nature of the cut-uncut profile, and therefore will have difficulty crossing small diameters curvatures as is explained in detail below.

SUMMARY OF THE INVENTION

The present invention is directed to a hypotube support catheter with a shapeable tip, such as for treating BTK, coronary, pediatric and other small blood vessels, from both antegrade and retrograde approaches. Such support catheters can also be used in larger blood vessels. The present invention provides a unique support catheter for supporting guidewire penetration through plaque inside blood vessels, during angioplasty procedures, to be followed by support catheter plaque penetration.

The device of the invention is aimed to improve the physician's technique and success in treating totally or partially blocked blood vessels, by providing a very flexible support catheter that provides high pushability and high torqueability, and allows tip bending and shaping to fit a patient-specific anatomy.

The above combined characteristics are achieved by cutting the hypotube with a series of cuts that result in multi-axis flexibility with very high pushability and torqueability, together with tip shaping and minimal risk of hypotube breaking. The cutting profile is achieved by intermittent cutting of the hypotube, while rotating and then advancing it, but not at the same time. At a first axial location, the metal hypotube is rotated at a desired rotational speed. At this axial location, cutting and un-cutting is performed intermittently, preferably at least twice in one full 360° hypotube rotation. The hypotube is then advanced axially to a second axial location and a second series of intermittent cutting and un-cutting is performed. This second circular cutting starts only after a phase shift of, for example, 45°. The next circular intermittent cutting starts again after another axial step and another phase shift. This phase shift provides multi-axis flexibility of the hypotube.

Manual plastic strain during catheter bending is feasible and safe, at any direction, if small axial steps between such circular cuttings are used. Significant total plastic strain due to bending forces, resulting in very small tip bending diameters, is possible without metal breaking.

The hypotube is preferably covered by a thin polymer jacket made from materials, such as PTFE (polytetrafluoroethylene), PEBAX (trade name for a polyether block amide) or nylon on its exterior, interior, or both. Such jackets can prevent blood leakage from the laser-cuts, and provide reduced friction for the passage of the guidewire through the support catheter.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
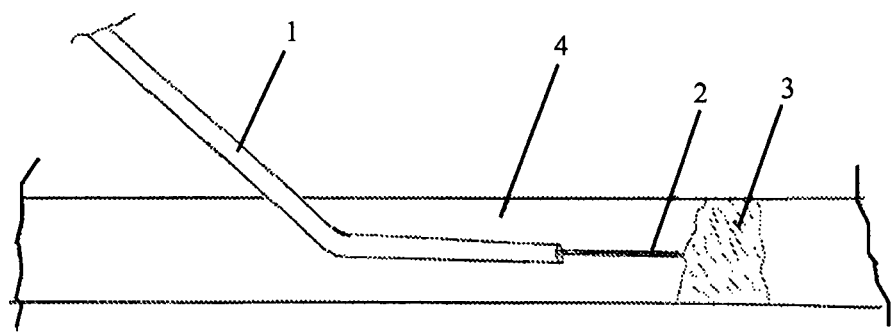
FIG. 1 is a simplified illustration of the support catheter of the invention inserted into an artery.

Reference is now made to FIG. 1, which illustrates a support catheter 1, constructed and operative in accordance with an embodiment of the present invention. Support catheter 1 can improve the physician's technique in treating blood vessel occlusions including BTK occlusions, and can be used to cross both new, soft plaque and old, hard plaque.

Support catheter 1 supports a guidewire 2 for penetration through plaque 3 inside a blood vessel 4, such as but not limited to, the femoral artery, during angioplasty procedures.

Figure 2:
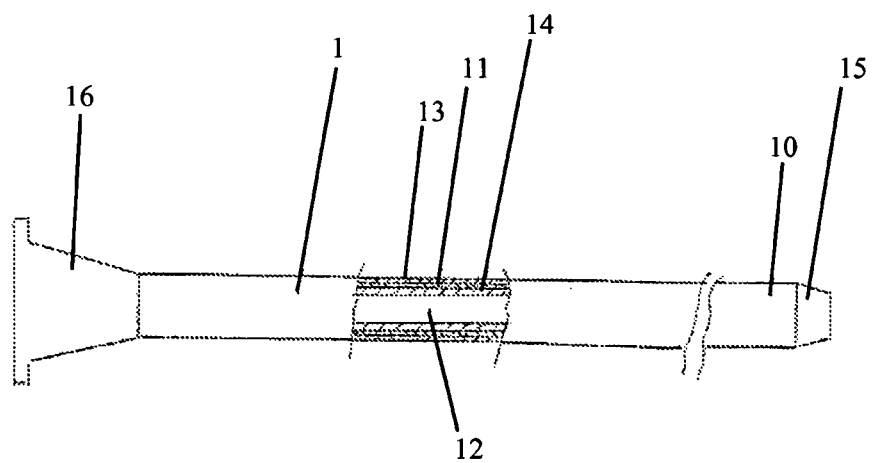
FIG. 2 is a simplified illustration of a preferred embodiment of the support catheter of the invention.

Reference is now made to FIG. 2. Support catheter 1 has a shapeable tip 10, which can be bent and otherwise shaped to fit any specific anatomy. Support catheter 1 has good multi-axis flexibility, which is required to lead the guidewire through tortuous and curved blood vessels. Support catheter 1 has good pushability to help the guidewire pass through hard calcified plaques, after which the support catheter also passes through. Support catheter 1 has good torqueability, which is required whenever the support catheter tip is not fully straight, and the guidewire protrusion needs to be aimed towards the plaque.

In accordance with an embodiment of the present invention, the above combination of characteristics is achieved by constructing support catheter 1 of a hypotube 11 that has a plurality of cuts 20 and an inner lumen 12 and distal tip 10. Cuts 20 are cut in a special profile, as described below, which achieves multi-axis flexibility with very high pushability and torqueability, together with the ability to shape distal tip 10 with minimal risk of hypotube breakage.

In an exemplary, non-limiting embodiment of the present invention, hypotube 11 is thin-walled, having an outside diameter of up to 6 Fr (2.0 mm), made from metal, such as, but not limited to, stainless steel, which can readily be cut by laser or other cutting tools.

Hypotube 11 may be covered by thin non-metal (e.g., polymer) jackets 13 and 14, made from materials, such as, but not limited to, PTFE, PEBAX or nylon on its exterior, interior, or both. Such jackets help prevent blood leakage from cuts 20, and provide reduced friction for the passage of the guidewire 2 through support catheter 1. One or both of jackets 13 and 14 may be formed into a distal tapered tip 15, preferably, but not necessarily, having a length of less than 2 mm.

A female luer connector 16 is connected to a proximal end of support catheter 1, which provides easy guidewire access and the possibility of using a standard injection syringe for contrast media injection and the like.

Figure 3:
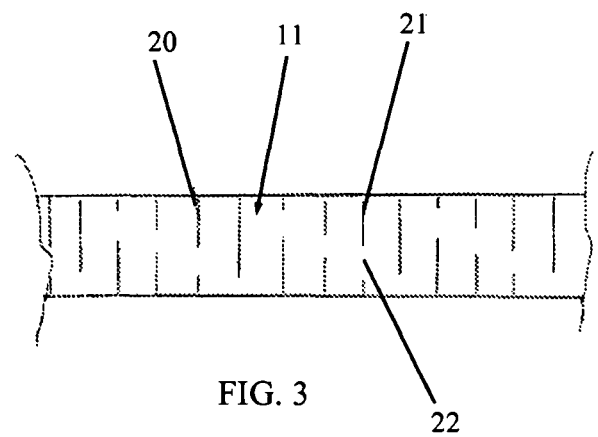
FIG. 3 is a simplified side view illustration of a preferred embodiment of few consecutives circular hypotube laser cuts, shifted by 45 degrees from each other.

Reference is now made to FIG. 3. In accordance with an embodiment of the invention, the cutting profile is based on intermittent cutting of hypotube 11, while rotating and advancing it, but not at the same time. At a first axial station, hypotube 11 is rotated at a desired rotational speed, while intermittently cuts 20 are made by a cutting operation (e.g., laser cuts) and an uncut portion 22 is left. The uncut portion 22 is preferably, but not necessarily, smaller than the cut section 20. Cut and uncut segments are made more than once in a full 360° circle, and preferably twice on every circle. For example, a cut of 120° and an uncut portion of 60°, performed twice in one full hypotube rotation, complete a full 360° circle.

Figure 4A:
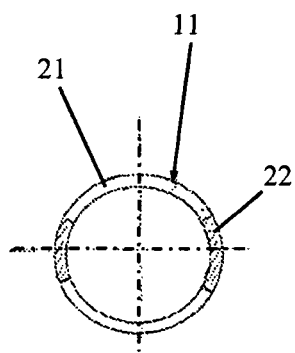
FIGS. 4A, 4B and 4C are frontal cross sectional views of different embodiments of a few consecutive circular hypotube laser cuts, shifted by 45° from each other.
Figure 4B:
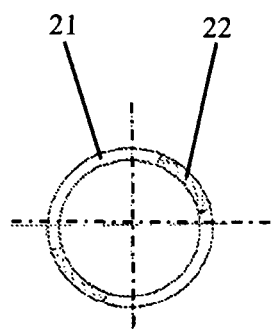
Figure 4C:
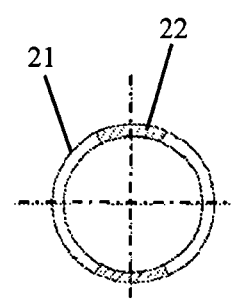

Hypotube 11 is then advanced axially by a small axial increment, for example, 0.2 mm, and another intermittent circular cutting operation is performed (e.g., 120° cut/60° uncut, done twice in full circle, in the above example). This second circular cutting starts only after a phase shift of preferably smaller than 90°, e.g., 45°. Subsequent intermittent circular cutting/uncutting operations with phase shift are then performed at a series of axial increments. FIGS. 4A, 4B and 4C illustrate different embodiments of a few consecutive circular hypotube laser cuts, shifted by 45° from each other. This phase shift provides multi-axis cutting and therefore multi-axis flexibility of the hypotube.

In another preferred embodiment of the invention, the intermittent circular cutting can have three, four or more cut slots and uncut sections instead of two, in one full hypotube circle. For example, the invention can be carried out with a 90° cut and 30° uncut performed three times in one circle, before an axial step, a phase shift and the start of new circular cut. The intermittent cuts and uncut portions can extend over some or all of the total axial length of the hypotube 11.

Figure 5:
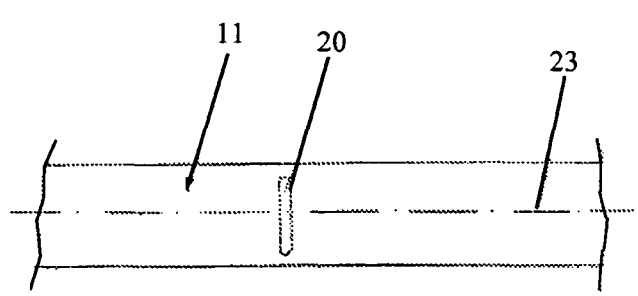
FIG. 5 is a simplified illustration of a circular intermittent laser cut done perpendicularly to the hypotube longitudinal axis.
Figure 6:
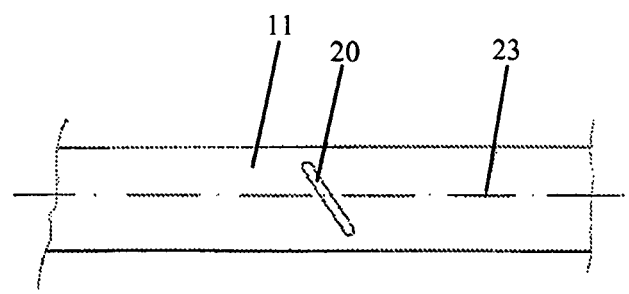
FIG. 6 is a simplified illustration of a circular intermittent laser cut done at an angle (spiral cut) to the hypotube longitudinal axis.

Comparing the support catheter of the invention to catheters cut/uncut in spiral advancement (like the one described in US Patent Application 2009/0275795), the catheter of the invention provides similar pushability and torqueability, but provides much better multi-axis flexibility, and safer tip bending, as is now explained with reference to FIGS. 5 and 6.

The bending moment needed to bend a beam or a bar is directly related to its moment of inertia "I" of the beam or bar. The larger the moment of inertia, the larger the moment needed to bend the device and the flexibility is lower. If the hypotube is cut and uncut intermittently, the uncut tube section can approximately be described as a beam. Beam moment of inertia is $I=BH^3/12$ (B=beam length, H=beam height). When the cut 20 is perpendicular to the tube axis 23, as in FIG. 5, the material left to resist the bending moment length B is only the length of the uncut sections in the specific cross section. When the cut 20 is not perpendicular to the tube axis 23, as in FIG. 6, only a small portion of the cut section is reduced from the length B, increasing the moment of inertia "I", and therefore the catheter stiffness and the resistance to bending, which means reduced flexibility.

The two parallel small uncut sections at every circle, together with a few small steps between every identical cut/uncut circles (same phase circles), divides the plastic strain across a few consecutive similar circles with the same cut angle phases. This creates a tip that is safe plastically (not just elastically) when it is bent to different tip shapes in every direction, while maintaining multi-direction flexibility.

Figure 7:
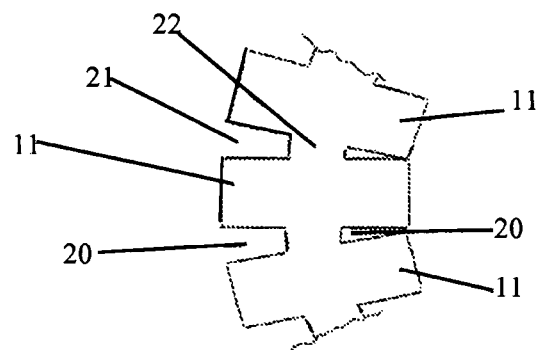
FIG. 7 is a simplified illustration of limited plastic reshaping the distal tip of the hypotube of the support catheter of the invention.

The safety-enhanced tip shaping can be further explained by referring to FIG. 7. Each segment with the same phase shift (in the above example with 45° phase shift, every 0.8 mm there will be the same circular cutting with same phase shift) can easily bend plastically until the gap made by the cut 20 between the two consecutive segments is closed. The gap size may be, for example, between 20 to 50 microns, such as when cut by laser. The size of the gap and the structure of the uncut section can provide a safety mechanism to bend the tip, creating plastic strain in the two uncut sections in every identical circle. The structure ensures that this plastic strain does not reach the breaking strain, because the strain is limited to the size of the gap between segments. After the portions have abutted each other, the strength of the segment and resistance to bending is dramatically increased, providing the user with a tactile indication not to increase the bend in order to avoid the potential risk of hypotube breakage.

To make the above clearer, using the abovementioned cutting profile, two parallel uncut sections 22 (or "beams" 22) made from 60° segments of the tube circumference, are able to slightly plastically bend without breaking, and the same pattern will appear again in just four circular steps, which are only 0.8 mm in distance from the first two "beams". In this way, several sections with the same pattern participate in the plastic re-shaping of the tip, limited by such factors as cut width, hypotube material, hypotube thickness, distance (step) between every two cut/uncut circles, and the uncut section length, for example.

Manual plastic strain due to bending is feasible and safe, at any direction, if small axial steps between circular cuttings, of about 0.2 mm, are used. Significant total plastic strain is due to bending forces. This results in very small catheter tip bending diameters, such as 2 mm bending diameter in a 1.0 mm catheter diameter, without metal breaking.

What is claimed is:

1. A support catheter comprising:
   a hypotube comprising an inner lumen, a distal tip and a longitudinal axis;
   wherein said hypotube is formed with a plurality of intermittent cuts and uncut portions located at least four axial stations along said hypotube, wherein at each axial station, a pair of cuts are separated by a pair of uncut portions, wherein the pair of cuts and the pair of uncut portions subtend a full 360° circle around a periphery of said hypotube perpendicular to the longitudinal axis such that each cut subtends 120° and each uncut portion subtends 60°, and at each adjacent axial station, spaced by an axial increment from a previous axial station, the pair of cuts and the pair of uncut portions are phase shifted with respect to the pair of cuts and pair of uncut portions of the previous axial station, there being a positive angle phase shift of 45° between adjacent axial stations over at least a portion of a length of said hypotube.

2. The support catheter according to claim 1, wherein said cuts and said uncut portions extend over at least some of a total axial length of said hypotube.

3. The support catheter according to claim 2, wherein said cuts and said uncut portions extend over the total axial length of said hypotube.

4. The support catheter according to claim 1, wherein said distal tip is bendable.

5. The support catheter according to claim 1, further comprising a non-metal jacket on an outer perimeter of said hypotube.

6. The support catheter according to claim 1, further comprising a non-metal jacket on an inner perimeter of said hypotube.

7. The support catheter according to claim 1, further comprising a non-metal jacket disposed in or on said hypotube and formed into a distal tapered tip.

8. The support catheter according to claim 1, further comprising a luer connector connected to a proximal end of said support catheter.

* * * * *